(12) United States Patent
Ford et al.

(10) Patent No.: US 6,497,870 B1
(45) Date of Patent: Dec. 24, 2002

(54) THERAPEUTIC USES OF IL-1 RECEPTOR ANTAGONIST

(75) Inventors: John Ford, San Mateo, CA (US); Alice Suk-Yue Ho, Union City, CA (US)

(73) Assignee: Hyseq, Inc., Sunnyvale, CA (US)

( * ) Notice: Subject to any disclaimer, the term of this patent is extended or adjusted under 35 U.S.C. 154(b) by 0 days.

(21) Appl. No.: 09/576,755

(22) Filed: May 22, 2000

(51) Int. Cl.$^7$ .................. A61K 45/00; A61K 38/00; C07K 14/00
(52) U.S. Cl. ................ 424/85.2; 514/2; 530/351
(58) Field of Search .................. 424/85.2; 514/2; 530/351

(56) References Cited

U.S. PATENT DOCUMENTS 5,922,573 A 7/1999 Boraschi et al.

FOREIGN PATENT DOCUMENTS

| WO | WO-0107840 | * | 2/2001 |
| WO | WO 01/42304 | | 6/2001 |
| WO | WO 01/42305 | | 6/2001 |

OTHER PUBLICATIONS

Evans, et al., "Mapping Receptor Binding Sites in Interleukin (IL)-1 Receptor Antagonist and IL-1β by Site-directed Mutagenesis," *J. of Biol. Chem.* 270:11477–11483 (1995).
Fang, et al., "Inhibitory Effect on Electroacupuncture on Murine Collagen Arthritis and Its Possible Mechanism," *In Vivo* 13:311–318 (1999).
Garbrecht, et al., "Long–term Growth of Human T Cell Lines and Clones on Anti–CD3 Antibody–Treated Tissue Culture Plates," *J. of Immunol. Meth.* 107:137–142 (1988).
Jourdan, et al., "Autocrine Function of Inducible Nitric Oxide Synthase and Cyclooxygenase-2 in Proliferation of Human and Rat Pulmonary Artery Smooth–Muscle Cells," *Am. J. Respir. Cell Mol. Biol.* 21:105–110 (1999).
Ju, et al., "Conversion of the Interleukin–1 Receptor Antagonist Into An Agonist by Site–specific Mutagenesis," *Proc. Natl. Acad. Sci. USA* 88:2658–2662 (1991).
Mitchell, et al., "Selectivity of Nonsteroidal Antiinflammatory Drugs as Inhibitors of Constitutive and Inducible Cyclooxygenase," *Proc. Natl. Acad. Sci. USA* 90:11693–11697 (1994).
Osaki, et al., "IFN–γ–Inducing Factor/IL–18 Administration Mediates IFN–γ and IL–12 Independent Antitumor Effects," *J. of Immunol.* 160:1742–1749 (1998).
Puren, et al., "Interleukin–18 (IFN–γ–inducing Factor) Induces IL–8 and IL–1β via TNF–α Production from Non–CD4+ Human Blood Mononuclear Cells," *J. Clin. Invest.* 101:711–721 (1988).
Rosak, et al., "Manipulation of Distinct NFκB Proteins Alters Interleukin–1β–induced Human Rheumatoid Synovial Fibroblast Prostaglandin $E_2$ Formation," *J. of Biol. Chem.* 271:31496–31501 (1996).

Antin et al., Recombinant Human Interleukin–1Receptor Antagonist in the Treatment of Steroid–Resistant Graft–Versus–Host Disease, *Blood* 84(4):1342–1348 (Aug. 15, 1994).
Bresnihan et al., Interleukin–1 Receptor Antagonist, *Emerging Therapies For Rheumatoid Arthritis* 24(3):615–628 (Aug. 1998).
Bresnihan, Treatment of Rheumatoid Arthritis with Interleukin 1 Receptor Antagonist, *Ann. Rheum. Dis.* 58:196–198 (1999).
Carson et al., A Fatal Cytokine–Induced Systemic Inflammatory Response Reveals a Critical Role for NK Cells, *J. Immunol.* 162:4943–4951 (1999).
Cohen, IL–12 Deaths: Explanation and a Puzzle, *Science* 270:908 (nov. 10, 1995).
Constantinesuc et al., Antibodies Against IL–12 Prevent Superantigen–Induced and Spontaneous Relapses of Experimetnal Autoimmune Encephalomyelitis, *J. Immunol.* 161:5097–5104 (1998).
Dinarello, Interleukin–18, *Methods* 19:121–132 (1999).
Dinarello, Interleukin–1, Interleukin–1 Receptors and Interleukin–1 Receptor Antagonist, *Inter. Rev Immunol.* 16:457–499 (1998).
Fadeel et al., Induction of Apoptosis and Caspase Activation in Cells Obtained from Familial Haemophagocytic Lymphohistiocytosis Patients, *British Journal Of Haematology* 106:406–415 (1999).
Fiorucci et al., NO–Aspirin Protects from T Cell–Mediated Liver Injury by Inhibiting Caspase–Dependent Processing of Th1–Like Cytokines, *Gastroenterlogy* 118:404–421 (2000).
Fisher et al., Initial Evaluation of Human Recombinant Interleukin–1 Receptor Antagonist in the Treatment of Sepsis Syndrome: A Randomized, Open–Label, Placebo–Controlled Multicenter Trial, *Critical Care Medicine* 22(1):12–21 (1994).
Fisher et al., Recombinant Human Interleukin 1 Receptor Antagonist in the Treatment of Patients with Sepsis Syndrome, *J. Amer. Med. Assoc.* 271(23): 1836–1843 (Jun. 15, 1994).
Gillespie et al., Interleukin–18: Perspectives on the Newest Interleukin, *Cytokine & Growth Factor Reviews* 9(2): 109–116 (1998).
Kiniwa et al., Recombinant Interleukin–12 Suppresses the Synthesis of Immunoglobulin E by Interleukin–4 Stimulated Human Lymphocytes, *J. Clin. Invest.* 90:262–266 (Jul. 1992).

(List continued on next page.)

Primary Examiner—Yvonne Eyler
Assistant Examiner—Janet L. Andres
(74) Attorney, Agent, or Firm—Marshall, Gerstein & Borun

(57) ABSTRACT

The present invention provides novel therapeutic methods of administering an amount of IL-1Ra to treat IL-18 related disorders. Specifically, the method involves treating IL-18 related disorders such as liver injury, hepatis, hemophagocytic lymphohistiocytosis, multiple sclerosis, tumors, cytotoxicity resulting from antitumor therapy, or other autoimmune disorders with a therapeutically effective amount of IL-1ra, and optionally measuring IFN-γ and IL-18 activity from human samples.

3 Claims, No Drawings

OTHER PUBLICATIONS

Kohno et al., IFN–γ–Inducing Factor (IGIF) is a Costimulatory Factor on the Activation Of Th1 but not Th2 Cells And Exerts its Effect Independently of IL–12, *J. Immunol.* 158: 1541–1550 (1997).

Lauwerys et al., Synergistic Proliferation and Activation of Natural Killer Cells by Interleukin 12 And Interleukin 18, *Cytokine* 11(11):822–830 (1999).

Lieberman et al., Natural Killer Cell Stimulatory Factor (NKSF) Augments Natural Killer Cell and Antibody–Dependent Tumoricidal Response Against Colon Carcinoma Cell Lines, *Journal of Surgical Research* 50: 410–415 (1991).

Micallef et al., Interferon–γ–Inducing Factor Enhances T Helper 1 Cytokine Production by Stimulated Human T Cells: Synergism With Interleukin–12 for Interferon–γ–Production, Eur. *J. Immunol.* 26: 1647–1651 (1996).

Okamura et al., Cloning of a New Cytokine that Induces IFN–γ Production by T Cells, *Nature* 378:88–91 (Nov. 2, 1995).

Okamura et al., Interleukin–18: A Novel Cytokine That Augments Both Innate and Acquired Immunity, *Advances in Immunology* 70: 281–312 (1998).

Okamura et al., Regulation of Interferon–γ Production by IL–12 And IL–18, *Current Opinion In Immunology* 10: 259–264 (1998).

Petereit et al., Interferon Gamma Production in Blood Lymphocytes Correlates With Disability Score in Multiple Sclerosis Patients, *Multiple Sclerosis* 6: 19–23 (2000).

Rep et al., Interferon (IFN)–β Treatment Enhances CD95 and Interleukin 10 Expression but Reduces Interferon–γ Producing T Cells in MS Patients, *Journal of Neuroimmunology* 96:92–100 (1999).

Takada et al., Oversecretion of IL–18 In Haemophagocytic Lymphohistiocytosis: A Novel Marker of Disease Activity, *British Journal of Haematology* 106: 182–189 (1999).

Tominaga et al., IL–12 Synergizes with IL–18 or IL–1β for IFN–γ Production from Human T Cells, *International Immunology* 12(2): 151–160 (1999).

Tsuji et al., Alleviation of Lipopolysaccharide–Induced Acute Liver Injury in *Propionibacterium acnes*–Primed IFN–γ–Deficient Mice by a Concomitant Reduction of TNF–α, IL–12, and IL–18 Production, *J. Immunol.* 162: 1049–1055 (1999).

Ushio et al., Cloning of the cDNA For Human IFN–γ–Inducing Factor, Expression in *Escherichia coli*, and Studies on the Biologic Acitivties of the Protein, *J. Immunol.* 156:4274–4279 (1996).

Wildbaum et al., Neutralizing Antibodies to IFN–γ–Inducing Factor Prevent Experimental Autoimmune Encephalomyelitis, *J. Immunol.* 161: 6368–6374 (1998).

* cited by examiner

SEQUENCE LISTING

```
<160> NUMBER OF SEQ ID NOS: 1

<210> SEQ ID NO 1
<211> LENGTH: 177
<212> TYPE: PRT
<213> ORGANISM: Homo sapiens

<400> SEQUENCE: 1

Met Glu Ile Cys Arg Gly Leu Arg Ser His Leu Ile Thr Leu Leu Leu
 1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60
```

-continued

```
Val Asn Leu Glu Glu Lys Ile Asp Val Val Pro Ile Glu Pro His Ala
 65                  70                  75                  80

Leu Phe Leu Gly Ile His Gly Gly Lys Met Cys Leu Ser Cys Val Lys
                 85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu
```

THERAPEUTIC USES OF IL-1 RECEPTOR ANTAGONIST

FIELD OF THE INVENTION

The present invention relates to novel therapeutic uses of interleukin-1 receptor antagonist for conditions involving elevated levels of interleukin-18, interleukin-12 or interferon-γ.

BACKGROUND

IL-1 receptor antagonist (IL-1Ra or IRAP) is a naturally occurring protein that inhibits the activity of the proinflammatory cytokine interleukin-1 (IL-1). The IL-1 pathway consists of the two agonists IL-1α and IL-1β, a specific activation system (IL-1 converting enzyme), a receptor antagonist (IL-1Ra) produced in different isoforms and two high affinity receptors. IL-1α and IL-1β bind to two distinct IL-1 receptor types, IL-1 receptor type I (IL-1RI) and IL-1 receptor type II (IL-1RII), both of which are members of the immunoglobulin superfamily of receptors. Both types of receptors are usually coexpressed, although type I is the predominant form in fibroblasts and T cells, while type II is preferentially expressed on B cells, monocytes and neutrophils. IL-1RI and IL-1RII have different affinities for the three ligands of the IL-1 family (IL-1α, IL-1β and IL-1Ra). In particular, IL-1Ra binds to the type I receptor with an affinity similar to that of IL-1α, while IL-1Ra binds to the type II receptor 100-fold less efficiently than the type I receptor. There is evidence indicating that IL-1 induced activities are mediated exclusively via the type I receptor, whereas the type II receptor has no signaling activity and inhibits IL-1 activities by acting as a decoy for IL-1.

IL-1Ra binds to the IL-1 receptor with affinity similar to that of IL-1 but has no IL-1-like activity, even at very high concentrations, and thus inhibits (antagonizes) the activity of IL-1. The purified IL-1Ra molecule has a molecular weight of approximately 25 kD and is believed to be glycosylated. An unglycosylated recombinant form of IL-1Ra that has a molecular weight of approximately 17 kD is commercially available from R&D Systems (Minneapolis, Minn.). IL-1Ra has limited sequence similarity to IL-1α and IL-1β at the amino acid level (19% and 26%, respectively). There appear to be at least two isoforms of IL-1Ra, including a soluble form and an intracellular form generated by an alternative splicing event. IL-1Ra appears to be produced by monocytes, macrophages, neutrophils and fibroblasts; keratinocytes and cells of epithelial origin produce almost exclusively the intracellular form. In humans, the gene for IL-1Ra has been localized to the long arm of chromosome 2, which is the same region where IL-1α and IL-1β, as well as IL-1RI and IL-1RII, are found.

Treatment of IL-1 related conditions through the administration of IL-1 Ra molecules has been extensively studied in both in vitro and animal models. These models include those for infection, local inflammation, acute or chronic lung injury, metabolic dysfunction, autoimmune disease, immune-mediated disease, malignant disease, and host responses. In addition, human recombinant IL-1Ra has been administered to humans in clinical trials for rheumatoid arthritis, septic shock, steroid resistant graft versus host disease, acute myeloid leukemia, and chronic myelogenous leukemia. [Dinarello et al., *Intern. Rev. Immunol.*, 16:457–499 (1998).] In these human clinical trials, IL-1Ra was not shown to significantly reduce mortality in humans with septic shock. [Fisher et al., *J.A.M.A.*, 271:1836–43 (1994).] Clinical trials have indicated that patients tolerate administration of human recombinant IL-1Ra well without serious adverse effects.

Interleukin-18 (IL-18) is a 18.3 kD cytokine which is a strong inducer of interferon-γ (IFN-γ). Even though IL-18 exhibits low sequence identity to the interleukin-1 (IL-1) family members (IL-1α, IL-1β, IL-1Ra), it is structurally similar to this family of cytokines. Particularly, IL-18 exhibits a 12β sheet structure that is common among IL-1 cytokine family members and shares features of the IL-1 like-signature sequences. This indicates that IL-18 is a structurally distinct cytokine compared to the IL-1 family. (See Gillespie and Horwood, Cytokine and Growth Factor Review, 9: 109–116, 1998).

The IL-18 receptor (IL-18R) was initially denoted as IL-1 receptor binding protein even though it does not bind IL-1α, IL-β, or IL-1Ra. It does however, transmit signals similar to that of IL-1R. Radiolabeled IL-18 binding studies have revealed the presence on IL-18R of high and low affinity sites for IL-18. The low affinity sites are normally available on IL-18R, while the high affinity binding sites become available when IL-18R is complexed with an accessory protein-like receptor. A soluble decoy receptor that binds IL-18 has also been identified, similar to what is observed in the IL-1 receptor system.

IL-18 is known to be expressed by activated macrophages, osteoblasts, keratinocytes, epithelial cells, pancreas cells, adrenal cells, skeletal muscle cells, liver cells, lung cells and unstimulated PBMC cells. The known functions of IL-18 include induction of IFN-γ expression in spleen cells such as T-cells, B-cells and NK cells, stimulation of T cell proliferation, enhancement of NK cell lytic cycle, enhancement of Fas ligand expression and function in T cells and NK cells, and induction of GM-CSF secretion. IL-18 also exhibits anti-viral and anti-microbial activity and suppresses tumor growth. IL-18 has also been associated with the progression of chronic inflammatory diseases including endotoxin shock, hepatitis, and autoimmune disease.

The biological activities of IL-18 are exerted in synergy with interleukin-12 (IL-12). The combination of these two cytokines are known to markedly enhance production of IFN-γ in T cells and B cells. In addition to IFN-γ, the combination of IL-12 and IL-18 increases production of IL-3, IL-6 and TNF. IL-18 has also been shown to potentiate IL-12-driven Th1 cell development. Studies have indicated that IL-12 will increase expression of IL-18 receptor, which may be the mechanism for this synergy. There is evidence that this synergistic effect is carried out in vivo as well as in vitro. (See Okumura et al., Advances in Immunology, 70: 281–312, 1998). IL-18 and IL-12 are structurally different, bind different receptors and transduce signals through different signaling components.

IL-12 is a pro-inflammatory cytokine which was initally characterized for its potent ability to induce production of IFNγ. IL-12 exhibits sequence homology to IL-6 and G-CSF. Unlike most cytokines, IL-12 is biologically active as a heterodimeric protein consisting of a heavy chain (p40) covalently associated with a lighter chain (p35). The cells which produce IL-12 include dendritic cells, macrophages, Langerhans cells, EBV-transformed B cells, neutrophils, keratinocytes, microglia and astrocytes.

IL-12 exhibits pleiotrophic effects on multiple lymphoid cell subsets including promoting the expansion of T cells, T lymphocytes and NK-lymphokine activated killer cells. In addition, IL-12 potentiates the cytolytic activity of NK cells and cytotoxic lymphocytes. Clinically, theses effects on the immune system result in enhanced host protection from infectious diseases and therefore IL-12 exhibits anti-bacterial, anti-microbial and anti-viral activity.

Antitumor activity is also induced by IL-12 enhancement of the host's natural immunity to tumorgenesis. IL-12 has also been shown to inhibit angiogenesis in tumor systems which prevents blood flow to the growing tumors. The antitumor effects are potentiated by synergism with IL-2 in vivo. Clinical studies have shown that administration of the combination of IL-12 and IL-2 significantly increases systemic production of IFNγ which leads to severe toxicity in the patient, resulting in shock and mortality.

The pro-inflammatory effects of IL-12 promote autoimmune diseases such as multiple sclerosis and arthritis. In addition, IL-12 promotes transplant rejection.

There exists a need in the art for new methods of treating conditions involving elevated levels or activity of IL-12 and IL-18.

SUMMARY OF THE INVENTION

The present invention provides novel methods of using compounds that inhibit or antagonize IL-1 receptor type I, preferably IL-1Ra of SEQ ID NO:1 or an active variant thereof, for treating a human suffering from an IL-18, IL-12, or IFN-γ related disorder, i.e., a disorder resulting from or exacerbated by elevated levels of or enhanced activity of IL-18, IL-12, or IFN-γ. Specifically excluded from the definition of such IL-18, IL-12, or IFN-γ disorders are conditions for which the contemplated dosage of IL-1Ra has already been demonstrated to be an effective treatment in humans.

According to one aspect of the invention, the novel methods of treatment comprise administering to a human an IL-1Ra polypeptide comprising the amino acid sequence of SEQ ID NO: 1, or a variant thereof that retains biological activity, in an amount effective to inhibit (either partially or completely) the activity of IL-18 and/or IL-12 in the human subject. Beneficial effects may even be provided by a dosage that provides partial inhibition of IL-18or IL-12 activity, e.g., approximately 90%, 80%, 70%, 60%, 50%, 40%, 30% or 20% inhibition compared to baseline.

The methods optionally further include a step of measuring IL-18, IL-12 and/or IFN-γ levels or activity in a tissue or fluid sample from the subject. Levels of or activity (e.g., proinflammatory activity) of IL-18 and/or IL-12 can be measured in any way known in the art, including by measuring circulating or local levels of IFNγ, NK cell activation, or serum IgE levels.

Another aspect of the present invention provides a method of treating a human diagnosed with an IL-18, IL-12 or IFN-γ related disorder by measuring circulating or local levels or activity of IL-12, IL-18, and/or IFN-γ in a tissue or fluid sample from the human subject, followed by treating with a therapeutically effective amount of a compound that antagonizes or inhibits IL-1R, preferably IL-1Ra or an active variant thereof. Such measurements may be carried out before or concurrently with the IL-1Ra treatment.

Yet a further aspect of the invention provides a method of monitoring IL-1R antagonist/inhibitor treatment of a human with an IL-18, IL-12 or IFN-γ related disorder by measuring circulating or local levels or activity of IL-12, IL-18, or IFN-γ in a tissue or fluid sample from the human subject. Such measurements may be carried out before, concurrently and/or after administering the therapeutically effective amount of IL-1R antagonist/inhibitor.

These novel therapeutic uses of IL-1Ra are specifically contemplated for IL-18 related disorders including endotoxin induced liver injury, hepatitis and haemophagocytic lymphocytosis. The therapeutic uses of IL-1Ra are also specifically contemplated for IL-12 related disorders including multiple sclerosis and IL-12 induced cytotoxicity resulting from antitumor therapy.

It is contemplated that therapeutic methods according to the invention include treating IL-12 or IL-18 related disorders by concurrent administration of IL-1Ra, or an active variant thereof, and a second therapeutic agent.

Another aspect of the invention provides a method of treating any inflammatory disease state mediated by IL-18 by administering to a subject in need thereof an amount of IL-1 Ra or an active variant thereof effective to inhibit IL-18 activity. Also provided are in vitro as well as in vivo methods of inhibiting IL-18 activity.

Numerous additional aspects and advantages of the invention will become apparent to those skilled in the art upon consideration of the following detailed description of the invention which describes presently preferred embodiments thereof.

DETAILED DESCRIPTION OF THE INVENTION

The present invention provides novel therapeutic uses for compounds that inhibit or antagonize IL-1 receptor type 1, preferably interleukin-1 receptor antagonist (IL-1Ra) or active variants thereof. Other compounds that inhibit or antagonize IL-1 receptor type include: antibody specific for IL-1 receptor type I, antibody specific for IL-1 receptor accessory protein, IL-1Hy1 (described in co-owned, concurrently filed U.S. patent application Ser. No. 09/576,008 and in prior related Int'l Application No. PCT/US99/04291 filed Apr. 5, 1999 (Int'l Publication No. WO 99/51744), the disclosures of all of which are incorporated by reference), and IL-1Hy2 (described in co-owned, concurrently filed U.S. patent application Ser. No. 09/578,458 and co-owned, concurrently filed Int'l Application No. PCT/US00/14144 filed May 22, 2000 (Int'l Publication No. WO 00/71719), the disclosures of all of which are incorporated by reference).

The therapeutic uses as described herein with respect to IL-1Ra and active variants thereof encompass disorders associated with IL-12, IL-18, or IFN-γ that are not involved in disease states wherein IL-1 receptor antagonist is known to be an effective treatment in humans, e.g., rheumatoid arthritis. In contrast, IL-1Ra has not been shown to be effective for treating septic shock. Human recombinant IL-1Ra has been administered to humans in clinical trials for rheumatoid arthritis, septic shock, steroid resistant graft-versus-host disease, acute myeloid leukemia, and chronic myelogenous leukemia. IL-1Ra has been tested in some animal models of disease including models for infection, local inflammation, acute or chronic lung injury, metabolic dysfunction, autoimmune disease, immune-mediated disease, malignant disease, and host responses.

Therapeutic uses as described herein encompass any and all IL-18 or IL-12 related/mediated disorders wherein the dosage of IL-1Ra that has been shown to be therapeutically effective in humans is different from the dosage contemplated herein (i.e., a dosage that provides partial or complete inhibition of IL-18 and/or IL-12 and/or IFN-γ activity). A relatively low dosage of IL-1Ra is expected to be effective for blocking IL-18 induced IFN-γ production as described herein. Specifically contemplated for treating rheumatoid arthritis are doses of IL-1Ra less than 70 mg/day, preferably less than 30 mg/day.

The present invention also provides methods for identification or diagnosis of patients suffering from IL-18 and/or IL-12 related disorders for whom IL-1Ra treatment would be suitable, as well as methods for monitoring IL-1Ra treatment of patients. Such methods, which involve measuring IL-18, IL-12 and/or IFN-γ activity in a tissue or fluid sample from the human subject, are contemplated for any and all disorders associated with IL-12, IL-18 or IFN-γ.

IL-18 Related Disorders

IL-18 has been found to have a variety of biological activities including the stimulation of activated T cell proliferation, enhancement of NK cell lytic activity, induction of IFNγ secretion, enhancement of Fas ligand expression and function, and stimulation of granulocyte-macrophage colony-stimulating factor (GM-CSF) production by activated T cells. IL-18 has been shown to counteract viral and intracellular infections and suppress tumor formation. However, IL-18 is also involved in the pathogenic progression of chronic inflammatory diseases, including endotoxin-induced shock, liver injury (including endotoxin-induced liver injury, hepatitis, biliary atresia and obesity-related fatty liver) and autoimmune diseases. Other disorders related to IL-18 production include meliodosis, purine nucleoside phosphorylase deficiency, increased susceptibility to *Leishmania major* and *Staphylococcus aureus* infection, hemophagocytic lymphohistiocytosis, mononucleosis, viral meningitis/encephalitis, bacterial meningitis/encephalitis and ischemia or ischemia/reperfusion injury.

Inflammation may result from infection with pathogenic organisms (including gram-positive bacteria, gram-negative bacteria, viruses, fungi, and parasites such as protozoa and helminths), transplant rejection (including rejection of solid organs such as kidney, liver, heart, lung or cornea, as well as rejection of bone marrow transplants including graft versus host disease (GVHD)), or from localized chronic or acute autoimmune or allergic reactions. Autoimmune diseases include acute glomerulonephritis; rheumatoid or reactive arthritis; chronic glomerulonephritis; inflammatory bowel diseases such as Crohn's disease, ulcerative colitis and necrotizing enterocolitis; granulocyte transfusion associated syndromes; inflammatory dermatoses such as contact dermatitis, atopic dermatitis, psoriasis; systemic lupus erythematosus (SLE), autoimmune thyroiditis, multiple sclerosis, some forms of diabetes, or any other autoimmune state where attack by the subject's own immune system results in pathologic tissue destruction. Allergic reactions include allergic asthma, chronic bronchitis, allergic rhinitis, acute and delayed hypersensitivity. Systemic inflammatory disease states include inflammation associated with trauma, burns, reperfusion following ischemic events (e.g. thrombotic events in heart, brain, intestines or peripheral vasculature, including myocardial infarction and stroke), sepsis, ARDS or multiple organ dysfunction syndrome. Inflammatory cell recruitment also occurs in atherosclerotic plaques.

Endotoxin Related Diseases

Endotoxin activation of the systemic inflammatory response leads to a number of disorders including bacterial and/or endotoxin-related shock, fever, tachycardia, tachypnea, cytokine overstimulation, increased vascular permeability, hypotension, complement activation, disseminated intravascular coagulation, anemia, thrombocytopenia, leukopenia, pulmonary edema, adult respiratory distress syndrome, intestinal ischemia, renal insufficiency and failure, and metabolic acidosis.

Liver Injury

Hepatitis represents liver disorders that are characterized by hepatic inflammation and necrosis that can be manifested as an acute or chronic condition. These liver disorders include virus-induced hepatitis such as hepatitis A, hepatitis B, hepatitis C (non-A, non-B hepatitis), hepatitis D, hepatitis E; toxin and drug induced hepatitis such as acetaminophohen hepatotoxicity, halothane hepatotoxicity, mehtyldopa hepatotoxicity, iaoniazid hepatotoxicity, sodium valproate hepatotoxicity, phenytion hepatotoxicity, chlorpromazine hepatotoxicity, amiodarone hepatotoxicity, amioidarone hepatotoxicity, erythromycin hepatotoxicity, oral contraceptive hepatotoxicity, 17,α-alkyl-substituted anabolic steroid hepatotoxicity and trimethoprim-sulfamethoxazole hepatotoxicity; cholestatic hepatitis; alcoholic hepatitis; autoimmune chronic active hepatitis; and T cell mediated hepatitis. Other conditions that cause liver injury include congenital bilary atresia, obesity-related fatty liver and the autosomal recessive disease heamophagocytic lymphohistiocytosis (HLH).

IL-18 induced IFN-γ plays a role in liver injury. IFNγ has been shown to mediate LPS-induced liver injury following *Propionibacterium acnes* infection as described in Tsuji et al. (J. Immunol. 162: 1049–55, 1999). Large number of macrophages and lymphocytes infiltrate the portal area in response to *P. acnes* infection which results in intrahepatic formation of granulomas. IFNγ knock out mice exhibited less macrophage infiltration and a reduction in the number and size of granulomas. Subsequent treatment with low doses of LPS caused massive hepatic necrosis and increased IL-12, IL-18 and TNF-α serum levels in the normal mice, while the knock out mice exhibited drastic decreases in IL-12, IL-18 and TNF-α serum levels. The addition of IFNγ neutralizing antibody also caused a decrease in IL-18 and IL-12 levels. This model of liver injury indicates that LPS-induced liver injury is associated with increased levels of IL-18, IL-12 and IFN-γ. Currently, a role for IL-1β is not known in this liver injury model. Since IL-1β is known to be induced by LPS, it is possible IL-1β also plays a role in the disorder. Treatment with IL-1Ra may modulate the severity of liver injury due to IL-18 induced IFN-γ production and IL-1β.

IL-18 has also been shown to be involved in the immunomediated hepatitis model where treatment with concavalin A induced hepatitis in mice as described by Fiorucci et al. (Gastroenterology 118: 404–21, 2000). In this model, CD+ Tcells and Th1-like cytokines cause Fas mediated liver cell death. Treatment with a nitric oxide derivative of aspirin protected against this cell death by reducing production of IFNγ, IL-18, IL-12, IL-1β and TNF-α. In addition, a neutralizing antibody to IL-18 caused a decrease in IFNγ production and reduced liver injury induced by conA.

HLH is a fatal autosomal recessive disease that manifests in early childhood. This disease is characterized by fever, hepatosplenomegaly, cytopenia and widespread infiltration of vital organs by activated lymphocytes and macrophages. Patients with HLH exhibit elevated serum levels of IL-18. IL-18 plays an important role in the induction of Th1 cells in HLH patients. (Takada et al., Br. J. Haematol. 106: 182–9, 1999).

IL-1Ra inhibits IL-18 induced production of IFNγ. In the models described above, the degree of IL-1β activity is not known. Since IL-1β is known to be induced by LPS, it is possible that IL-1β also play a role in the pathogenicity of these conditions. The presence of the appropriate amount of IL-1Ra may modulate the severity of the disease states due to both IL-18 induced IFNγ production and IL-1β.

IL-12 Related Disorders

IL-12 is known to potentiate IFNγ production, and the cytolytic activity of NK cells and cytotoxic T lymphocytes. These immunomodulatory effects have implicated a role for IL-12 in therapies for cancer and infectious disease. However, these same therapeutic effects can also promote autoimmune diseases and chronic inflammatory conditions such as multiple sclerosis, transplant rejection and cytotoxicity.

IL-12 and IFN-γ are involved in the pathogenesis of multiple sclerosis (MS). In the experimental allergic encephalomyelitis animal model (EAE), the demyelinating effect on the central nervous system is carried out similar to that in humans suffering from MS. Currently, IFNβ is used to treat MS. The mechanism of IFNβ treatment may be to decrease the number of IFNγ producing T cells in MS patients. (Rep et al., J. Neuroimmunol. 96:92–100, 1999). In addition, IFNγ production in blood lymphocytes was found to correlate with disability score in MS patients. (Petcreit et al., Mult. Scler. 6: 19–23, 2000). Antibodies against IL-12 were found to prevent superantigen-induced and spontaneous relapses of EAE in mice (Constantineseu et al., J. Immunol. 161: 5097–5104, 1998). All these studies point to the involvement of IL-12 induced IFNγ production in the progression of MS in human patients. Therefore, IL-1Ra treatment to reduce IFNγ production may be an useful therapy for MS patients.

The combination of IL-12 and IL-2 has synergistic antitumor activity in vivo. However, in clinical trials the combination resulted in significant toxicity and subsequently shock and mortality. (Cohen, Science 270: 908 1995). In a murine model investigated by Carson et al. (J. Immunol., 162: 4943–5, 1999) determined that the fatal systemic inflammatory response was NK cell dependent but not related to other effector molecules in the system such as IL-1, TNF-α, and IFNγ. Since IL-1Ra inhibits IL-12 induced IFN-γ production is expected to inhibit other biological activities of IL-12 such as NK cell cytolytic activity. Inhibition of NK cell activity, through IL-1Ra administration, may reduce toxicity resulting from IL-12 antitumor treatment.

Measures of Effectiveness of IL-1Ra Treatment

The effect of IL-1Ra on IL-12 and/or IL-18 activity in the disorder may be determined by measuring the biological activities of these cytokines. Both IL-12 and IL-18 are known to induce IFNγ production in T cells. In addition to IFN-γ, the combination of IL-12 and IL-18 increases production of IL-3, IL-6 and TNF. Treatment with IL-1Ra is expected to reduce IFNγ production induced by IL-12 and IL-18. Circulating or local levels of IFNγ in tissue or fluid samples from patients treated with IL-1Ra will be an indication of the therapeutic effects of IL-1Ra on the IL-18 and IL-12 related disorders. Tissue samples include tissue samples from an area involved in inflammation or other disease. Fluid samples include, for example, whole blood, plasma, serum, cerebrospinal fluid, synovial fluid, peritoneal fluids (including lavage fluids or exudate), pleural fluids (including lavage fluids or exudate), wound fluids (including lavage fluids or exudate).

Furthermore, IL-12 is known to activate NK cells and to decrease serum IgE levels. These assays may also be used to measure the effectiveness of IL-1Ra treatment for IL-12 related disorders. The NK cell cytolytic activity in patients treated with IL-1Ra can be assayed by measuring patient's blood samples ability to lyse colon carcinoma or lymphoma cells in vitro. (Lieberman et al., J. Sur. Res., 50: 410–415, 1992) In addition, the serum levels of IgE from patients treated with IL-1Ra can be measured to determine the effectiveness of treatment for IL-12 related disorders. (Kiniwa et al. J. Clin. Invest., 90: 262–66, 1992)

To treat the IL-18 and/or IL-12 related disorders, IL-1Ra will be administered to patients suffering from said disorders in an amount effective to inhibit the activity of IL-18 and/or IL-12. As used herein, the term "IL-1 receptor antagonist (IL-1Ra)" refers to any polypeptide comprising the amino acid sequence of SEQ ID NO: 1 or an active variant thereof.

The term "variant" (or "analog") as used herein refers to any polypeptide differing from naturally occurring polypeptides by amino acid insertions, deletions, and substitutions, created using, e g., recombinant DNA techniques. Variants that comprise amino acid sequence having at least about 70%, about 75%, about 80%, about 85%, about 90%, about 95%, or higher sequence identity to SEQ ID NO: 1, and that retain the desired biological activity of SEQ ID NO: 1, are contemplated in the uses according to the present invention. Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence. Guidance can also be provided by various three-dimensional protein modeling programs known in the art. In general, conservative substitutions are expected to provide a variant that retains biological activity of wild type polypeptide.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

Pharmaceutical Formulations and Routes of Administration

Recombinant human IL-1Ra is commercially available from R& D Systems (Minneapolis, Minn.). IL-1Ra polypeptide or other composition of the present invention (from whatever source derived, including without limitation from recombinant and non-recombinant sources) may be administered to a patient in need, by itself, or in pharmaceutical compositions where it is mixed with suitable carriers or excipient(s) at doses to treat or ameliorate IL-12 and/or IL-18 and/or IFN-γ related disorders. Such a composition may optionally contain (in addition to protein or other active ingredient and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFN, G-CSF, thrombopoietin, stem cell factor, and erythropoietin. In further compositions, proteins of the invention may be combined with other agents beneficial to the treatment of IL-12 and/or IL-18 related diseases. These agents include various growth factors such as epidermal growth factor (EGF), platelet-derived growth factor (PDGF), transforming growth factors (TGF-α and TGF-β), insulin-like growth factor (IGF), as well as cytokines described herein.

The pharmaceutical composition may further contain other agents which either enhance the activity of the IL-1Ra or other active ingredient or compliment its activity or use in treatment. Such additional factors and/or agents may be included in the pharmaceutical composition to produce a synergistic effect with IL-1Ra, or to minimize side effects.

As an alternative to being included in a pharmaceutical composition of the invention including an IL-1Ra polypeptide, a second protein or a therapeutic agent may be concurrently administered with the IL-1Ra polypeptide (e.g., at the same time, or at differing times provided that therapeutic concentrations of the combination of agents is achieved at the treatment site). Techniques for formulation and administration of the compounds of the instant application may be found in "Remington's Pharmaceutical Sciences," Mack Publishing Co., Easton, Pa., latest edition. A therapeutically effective dose further refers to that amount of the compound sufficient to result in amelioration of symptoms, e.g., treatment, healing, prevention or amelioration of an IL-12 and/or IL-18 related disorder, or an increase in rate of treatment, healing, prevention or amelioration of an IL-12 and/or IL-18 related disorder. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

In practicing the method of treatment, a therapeutically effective amount of protein or other active ingredient of the present invention is administered to a mammal having an IL-12 and/or IL-18 related disorder to be treated. IL-1Ra polypeptide or other active ingredient of the present invention may be administered in accordance with the method of the invention either alone or in combination with other therapies such as treatments employing cytokines, lymphokines or other hematopoietic factors. When co-administered (i.e., concurrently administered) with one or more cytokines, lymphokines or other hematopoietic factors, IL-1Ra or other active ingredient of the present invention may be administered either simultaneously with the cytokine(s), lymphokine(s), other hematopoietic factor(s), thrombolytic or anti-thrombotic factors, or sequentially (i.e., before or after). If administered sequentially, the attending physician will decide on the appropriate sequence of administering IL-1Ra polypeptide or other active ingredient of the present invention in combination with cytokine(s), lymphokine(s), other hematopoietic factor(s), thrombolytic or anti-thrombotic factors.

Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of IL-1Ra or other active ingredient of the pharmaceutical composition can be carried out in a variety of conventional ways, such as oral ingestion, inhalation (e.g. in an aerosolized or nebulized formulation for delivery to the lungs), topical application or cutaneous, subcutaneous, intraperitoneal, parenteral or intravenous injection. Intravenous administration to the patient is preferred.

Alternately, one may administer the compound in a local rather than systemic manner, for example, via injection of the compound directly into an affected tissue, often in a depot or sustained release formulation. Furthermore, one may administer the drug in a targeted drug delivery system, for example, in a liposome coated with a specific antibody, targeting the affected tissue. The liposomes will be targeted to and taken up selectively by the afflicted tissue.

Compositions/Formulation

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of IL-1Ra or other active ingredient of the present invention is administered orally, IL-1Ra or other active ingredient of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% IL-1Ra polypeptide or other active ingredient of the present invention, and preferably from about 25 to 90% IL-1Ra or other active ingredient of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of I1-1Ra polypeptide or other active ingredient of the present invention, and preferably from about 1 to 50% IL-1Ra polypeptide or other active ingredient of the present invention.

When a therapeutically effective amount of IL-1Ra polypeptide or other active ingredient of the present invention is administered by intravenous, cutaneous or subcutaneous injection, IL-1Ra polypeptide or other active ingredient of the present invention will be in the form of a pyrogen-free, parenterally acceptable aqueous solution. The preparation of such parenterally acceptable protein or other active ingredient solutions, having due regard to pH, isotonicity, stability, and the like, is within the skill in the art. A preferred pharmaceutical composition for intravenous, cutaneous, or subcutaneous injection should contain, in addition to IL-1Ra polypeptide or other active ingredient of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein or other active ingredient stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the active ingredients of the invention may be provided as salts with pharmaceutically compatible counterions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The pharmaceutical composition of the invention may be in the form of a complex of the protein(s) or other active ingredient of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention. The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithins, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The amount of IL-1Ra or other active ingredient of the present invention in the pharmaceutical composition of the present invention will depend upon the nature and severity of the condition being treated, and on the nature of prior treatments which the patient has undergone. Ultimately, the attending physician will decide the amount of IL-1Ra or other active ingredient of the present invention with which to treat each individual patient. Initially, the attending physician will administer low doses of IL-1Ra or other active ingredient of the present invention and observe the patient's response. Larger doses of protein or other active ingredient of the present invention may be administered until the optimal therapeutic effect is obtained for the patient, and at that point the dosage is not increased further. It is contemplated that the various pharmaceutical compositions used to practice the method of the present invention should contain about 0.01 µg to about 100 mg (preferably about 0.1 µg to about 10 mg, more preferably about 0.1 µg to about 1 mg) of IL-1Ra or other active ingredient of the present invention per kg body weight.

Compositions of the present invention include therapeutic method administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the affected tissue. Therapeutically useful agents other than IL-1Ra or other active ingredient of the invention which may also optionally be included in the composition as described above, may alternatively or additionally, be administered simultaneously or sequentially with the composition in the methods of the invention. Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amount is well within the capability of those skilled in the art, especially in light of the detailed disclosure provided herein. For any compound used in the method of the invention, the therapeutically effective dose can be estimated initially from appropriate in vitro assays. For example, a dose can be formulated in animal models to achieve a circulating concentration range that can be used to more accurately determine useful doses in humans. For example, a dose can be formulated in animal models to achieve a circulating concentration range that includes the $IC_{50}$ as determined in cell culture (i.e., the concentration of the test compound which achieves a half-maximal inhibition of IL-18 and/or IL-12 induced IFN-$\gamma$ production). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p. 1. Dosage amount and interval may be adjusted individually to provide plasma levels of the active moiety which are sufficient to maintain the desired effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%. In cases of local administration or selective uptake, the effective local concentration of the drug may not be related to plasma concentration.

An exemplary dosage regimen for IL-1Ra will be in the range of about 0.01 to 100 mg/kg of body weight daily, with the preferred dose being about 0.1 to 25 mg/kg of patient body weight daily, varying in adults and children. Dosing may be once daily, or equivalent doses may be delivered at longer or shorter intervals.

The amount of composition administered will, of course, be dependent on the subject being treated, on the subject's age and weight, the severity of the affliction, the manner of administration and the judgment of the prescribing physician.

Previous clinical trials have determined that administration of IL-1Ra is well tolerated and does not cause serious side effects. For example, in patients suffering from rheumatoid arthritis, 30, 75, or 150 mg/day of recombinant IL-1Ra was self-administered as a single subcutaneous injection at the site of arthritis. This treatment caused a dose dependent reduction in the number of swollen joints and overall patient scores; decrease in C-reactive and sedimentation rates; and 50% reduction in new bone erosions. (See Brenihan, Ann. Rheum. Dis. 58:196–198, 1999).

In patients suffering from septic shock, IL-1Ra was administered as a loading bolus of 100 mg followed by 3 day infusion of 17, 67, or 133 mg/hr of IL-1Ra. In Phase II clinical trials, a dose dependent decrease in mortality was observed where 44% mortality in patients receiving the lowest dose and 16% mortality in group receiving the highest dose. (Fisher et al., Crit. Care Med. 22: 12–21, 1994). In further Phase III clinical trials, however, no statistically significant reduction in mortality was observed with IL-1Ra treatment.

Patients exhibiting graft-versus-host disease received 400–3400 mg/day of IL-1Ra continuously every 24 hours for 7 days as intervenous infusions. This treatment resulted in an improvement in 16 out of 17 patient as measured by an organ specific acute disease scale. (Antin et al., Blood 84: 1342–48, 1994).

Packaging

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

EXAMPLE 1

Inhibition of IL-18 Stimulated IFN-γ Production by IL-1Ra

Human lymphocytes (PBMC) were isolated from peripheral blood of healthy volunteer donors from Stanford University Blood Center by Ficoll-Hypaque density gradient separation as described in *Current Protocols in Immunology*. (Ch 7, John Wily, 1998). Immediately after isolation, the PBMC cells were washed twice with growth media (RPMI-1640 supplemented with 10% fetal bovine serum), then seeded at $3 \times 10^5$ cells per well on a 96 well culture plate.

The PBMC cells were stimulated by adding anti-CD3 antibody (R&D Systems) to a final concentration of 0.5 µg/ml. At the time of stimulation, the wells were also treated with a 100 ng/ml human recombinant IL-18 (R&D Systems) for 36 hours at 37° C. at 5% $CO_2$. A portion of the wells on each plate (triplicates) were untreated to served as a measure of background levels of IFNγ produced by stimulated PBMC cells. IL-18treatment causes the PBMC cells to increase production of IFN-γ relative to the background levels.

In order to determine if IL-1Ra had an effect on IL-18 stimulated IFNγ production, 0.01× to 1.0×fold concentration of IL-1Ra [R&D Systems, cat. no. 280-RA] (relative to IL-18 concentration) was added in combination with 100 ng/ml IL-18 at the time of PBMC cell stimulation. After the 36 hour stimulation, the culture plates were centrifuged at 4000 rpm for 5 minutes to remove cellular debris. The concentration of IFNγ in the stimulated PBMC cell supernatants was quantified with R&D Systems Quantikine IFNγ ELISA kit according to the manufacturer's instructions.

Treatment with IL-18 resulted in an elevation of PBMC production of IFNγ relative to basal levels. The relative increase in IFNγ production varied between donors but was consistently significantly increased compared to basal levels. The presence of IL-1Ra during stimulation consistently resulted in a dose dependent decrease in IL-18 induced IFNγ production. The low concentration of IL-1Ra (0.01-fold) caused a 70% decrease, while higher concentrations of 0.1-fold and 1.0-fold IL-1Ra caused complete (100%) inhibition of IL-18 induced IFNγ production. IL-1β induced IFN-γ in a sub-set of donor samples. (Oshio et al., J. Immunol. 156: 4274–79, 1996; Tominaga et al., Int. Immunol. 12: 151–60, 2000). In those donor samples in which IFNγ production is unaffected by IL-1β treatment, IL-1Ra consistently reduces IL-18 induced IFNγ production. This indicates that IL-1Ra inhibition of IL-18 induced IFN-γ production is acting independently of IL-1β.

EXAMPLE 2

Inhibition of IL-18 Stimulated IFNγ Production by Blocking Antibodies

Human lymphocytes (PBMC) were isolated and stimulated with IL-18 as described in Example 1. At the time of stimulation, the PBMC cells were also treated with a blocking antibody (IL-18 receptor antibody, IL-1 receptor accessory protein antibody, IL-1 receptor type I antibody or IL-1 receptor type II antibody) in addition to 100 ng/ml of IL-18. After the 36 hour stimulation, the culture plates were centrifuged at 4000 rpm for 5 minutes to remove cellular debris. The concentration of IFNγ was measured with the Quantikine IFNγ ELISA kit as described in Example 1.

IL-18 stimulation of PBMC cells resulted in increase in IFNγ production relative to background levels. The addition of 50 μg/ml of anti-human IL-1 receptor type I monoclonal antibody (R&D Systems cat no. MAB269) significantly decreased IL-18 induced IFNγ production by 100%, returning production to that of untreated PBMC cells. Treatment with a lower concentration of IL-1 receptor type I monoclonal antibody (5 μg/ml) had no effect on IL-18 induced IFNγ production. Monoclonal antibodies to IL-1 receptor type II (R&D Systems cat. no. MAB263), at both low (5 μg/ml) and high (50 μg/ml) concentrations did not have an effect on IL-18 induced IFNγ production. The addition of 20 μg/ml of IL-18 receptor blocking monoclonal antibody (R&D Systems cat no. MAB318) completely abolished (100%) IFNγ production by PBMC cells. Similar to treatment with IL-1 receptor type I monoclonal antibody, the addition of anti-receptor accessory protein polyclonal antibody (R&D Systems cat no. AF676; 10 μg/ml) significantly decreased (100%) IL-18 induced IFNγ production to levels similar to that of unstimulated PBMC cells.

These results indicate that compounds which antagonize the action of the IL-1 receptor inhibit IL-18 activity, as measured by induction of IFNγ production.

EXAMPLE 3

Inhibition of IL-12 Stimulated IFNγ Production by IL-1 Ra

Human lymphocytes (PBMC) were isolated as described in Example 1. Immediately after isolation, the PBMC cells were washed two times with culture media (RPMI-1640 supplemented with 10% fetal bovine serum) prior to seeding at $3 \times 10^5$ cells/well on a 96 well culture plate. The PBMC cells were stimulated with a final concentration of 0.5 μg/ml anti-CD3 monoclonal antibody. All but 1 well of PBMC cells was incubated with 100 ng/ml of IL-12 (R&D Systems) for 36 hours at 37° C. at 5% $CO_2$.

To determine if IL-1Ra had an effect on IL-12 induced IFNγ production in PBMC cells, at the time of stimulation the PBMC cells were treated with 10× to 100×fold concentration of IL-1Ra [R&D Systems cat no. 280-RA] (relative to IL-12 concentration). After the 36 hour stimulation, the culture plate was centrifuged at 4000 rpm for 5 minutes to remove cellular debris. The concentration of IFNγ in the supernatant was measured with the Quantikine IFNγ ELISA kit according to the manufacturer's instructions. The stimulation with IL-12 resulted in increased production of IFNγ relative to background levels. The addition of IL-1Ra resulted in an approximately 66% decrease in IL-12 induced IFNγ production at all concentrations tested.

EXAMPLE 4

IL-1Ra Comparative Inhibition of IL-1β Induced $PGE_2$ Production

Normal human dermal fibroblasts (NHDF) (Clonetics) were plated at $2 \times 10^4$ cells per well in a 96-well plate. After 24 hours, the cells were incubated with fresh growth media (Clonetics) containing 25 pg/ml recombinant human IL-1β for 16 h. To study the inhibition of IL-1β stimulated $PGE_2$ release by IL-1Ra, the cells were treated with increasing concentrations of IL-1Ra (1-fold to 1000-fold) together with IL-1β. The supernatants were then collected and cell debris was removed by centrifugation. The amount of $PGE_2$ in the supernatants was determined by ELISA using the $PGE_2$ assay system (R&D Systems) according to the manufacturer's protocol. Triplicate samples were performed for each reaction. IL-1Ra inhibited IL-1β induced $PGE_2$ production in a dose dependent manner. Complete inhibition is seen at about 100 fold excess of IL-1Ra.

In this $PGE_2$ assay (a classical IL-1 activity assay), it took about 100 fold molar excess of IL-1Ra to get complete inhibition of IL-1 activity. In contrast, it appears that IL-1Ra is able to exert its inhibitory activity even more potently in the IL-18 system than in the IL-1 system. (Compare Example 1). IL-1Ra appears 10,000 to 100,000 times more potent for blocking IL-18 activity and IFN-γ production compared to the dose needed to effectively block IL-1β activity.

Numerous modifications and variations of the above-described invention are expected to occur to those of skill in the art. Accordingly, only such limitations as appear in the appended claims should be placed thereon.

What is claimed is:

1. A method of inhibiting IFN-γ production induced by IL-18 in a human suffering from a viral infection by administering to said human a polypeptide of SEQ ID NO: 1 effective to inhibit IL-18 induced IFN-γ production, wherein said human exhibits elevated levels of IL-18, and wherein IL-1 β-induced inflammation is not inhibited.

2. The method of claim 1, wherein said human is suffering from hepatitis.

3. A method of inhibiting IFN-γ production induced by IL-18 in a human suffering from hemophagocytic lymphohistiocytosis (HLH) by administering to said human a polypeptide of SEQ ID NO: 1 effective to inhibit IL-18 induced IFN-γ production, wherein said human exhibits elevated levels of IL-18, and wherein IL-1 β-induced inflammation is not inhibited.

* * * * *